United States Patent [19]

Herlitze

[11] Patent Number: 4,951,686
[45] Date of Patent: Aug. 28, 1990

[54] COLOR MARKS ON CATHETER GUIDE WIRE

[75] Inventor: Gerhard Herlitze, Baunatal, Fed. Rep. of Germany

[73] Assignee: B. Braun-SSC AG, Emmenbrucke, Switzerland

[21] Appl. No.: 333,800

[22] Filed: Apr. 3, 1989

Related U.S. Application Data

[63] Continuation of Ser. No. 823,465, Jan. 28, 1986, abandoned.

[30] Foreign Application Priority Data

Feb. 26, 1985 [DE] Fed. Rep. of Germany ....... 3506750

[51] Int. Cl.⁵ ............................................. A61B 5/00
[52] U.S. Cl. ..................................... 128/772; 604/280
[58] Field of Search .................. 128/772, 656–658, 128/145; 604/280–282, 164–170; 29/DIG. 13, 24; 148/45, 128, 131, 134, 154; 266/129

[56] References Cited

U.S. PATENT DOCUMENTS

| | | | |
|---|---|---|---|
| 2,317,211 | 4/1943 | Nelson | 148/128 |
| 3,399,668 | 9/1968 | Lundgren | 604/280 X |
| 3,469,829 | 9/1969 | Fujita et al. | 148/131 |
| 3,885,561 | 5/1975 | Cami | 604/280 X |
| 4,001,054 | 1/1977 | Makepeace | 128/145 X |
| 4,003,369 | 1/1977 | Heilman et al. | 128/772 |
| 4,279,252 | 7/1981 | Martin | 604/280 X |
| 4,307,723 | 12/1981 | Finney | 604/281 X |
| 4,483,688 | 11/1984 | Akiyama | 604/265 |
| 4,534,363 | 8/1985 | Gold | 604/265 X |
| 4,682,607 | 7/1987 | Vaillancourt et al. | 128/772 |

*Primary Examiner*—Max Hindenburg
*Attorney, Agent, or Firm*—Kenyon & Kenyon

[57] ABSTRACT

For producing annular color marks on a spirally shaped catheter guide wire, a guide wire is selectively heated within a tempering range of 200° C. to 360° C. at the points provided for the color marks so that permanent temper colorations of the steel are left at said points. The advantage involved therewith is that color marks may be produced by neither removing nor applying material, and the contour of the guide wire is not changed. Further, no foreign material adhering to the guide wire may get into the body of the patient.

11 Claims, 1 Drawing Sheet

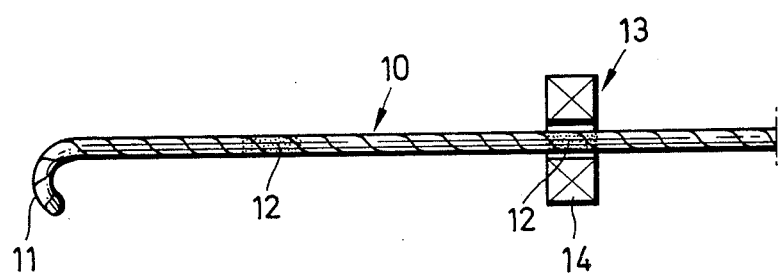

COLOR MARKS ON CATHETER GUIDE WIRE

This application is a continuation of application Ser. No. 823,465, filed Jan. 28, 1986, now abandoned.

BACKGROUND OF THE INVENTION

The invention relates to a process for producing color marks on a catheter guide wire of steel, to an apparatus for performing the process, and to a catheter guide wire of steel provided with color marks.

It has been known to use for the introduction of a catheter into a human body a metallic guide wire which imparts rigidity to the catheter and which, upon the introduction of the catheter is removed therefrom. Said leading-in technique is the so-called Seldinger technique, the respective guide wires being called Seldinger guide wires. To ensure that the guide wire is flexible enough to adapt itself to the contours of the blood vessels, it is made of one or more spirally wound leads. The guide wire also may include a core of longitudinally extending leads.

The known guide wires are provided with length marks allowing a determination of the length of the marking wire already introduced into the human body. The length marks are produced by printing, stamping or by laser beams, with the resultant disadvantage that the produced printing marks are prominent, or, in case of the laser beams, recessed. If printing ink is used, it is deposited between the helical turns sticking them together. Moreover, the printing ink may peel off if the guide wire is deformed. If the color marks consist of a pasted embossing sheet, the latter only adheres to the narrow circumferential surface of the spiral wire. Due to the small adhesive face, the embossing sheet may easily peel off. Further, marks are also applied by etching the spiral wire. Yet, in spite of repeated rinsings, residues of the etching agent may be left between the spiral turns or between the turns and the core.

SUMMARY OF THE INVENTION

It is the object of the invention to provide a process of the above mentioned kind which may be used without applying foreign material and without influencing the outer contour of the guide wire, while ensuring that no foreign material is left at the guide wire.

The process of the invention is characterized by a selective heating of the points provided for the color marks, at a temperature at which a permanent temper color is obtained.

The idea underlying the invention is to utilize the temper color of the guide wire steel for producing color marks. Marking rings of different colors may be caused by heat action. The process being practicable in a simple manner, is accompanied by the great advantage that the contour of the guide wire does not change and that no material is removed nor is any foreign material applied. By tempering the steel, the marking rings are colored permanently. The guide wire may be sterilized by simple means, it may be kept sterile, and the risk that foreign materials penetrate into the patient's body is excluded.

Preferably, heating is effected at a temperature between about 200° C. and 300° C. To obtain marks of different colors, various points may be heated at different temperatures.

A device for performing the process of the invention comprises an annular inductive heating means which encloses a guide wire section. Heating is effected selectively in the guide wire section present in the heating means.

Upon heating said section to the desired temperature, the guide wire is advanced so that another section thereof gets into the range of the heating means. It is also possible to serially arrange a number of heating means which simultaneously act on several sections of the guide wire.

A guide wire provided with color marks according to the process of the instant invention is characterized in that the color marks are temper colors of steel.

BRIEF DESCRIPTION OF THE DRAWING

The drawing shows a side view of the catheter guide wire on which color marks are produced.

DESCRIPTION OF THE PREFERRED EMBODIMENTS

With reference to the sole FIGURE of the drawing, one embodiment of the invention will be now explained hereunder in more detail.

The guide wire 10 consists of an elongated strand of at least one spirally wound wire having turns of a pitch due to which adjacent turns are in mutual contact. Further, the guide wire includes a (non-illustrated) core. The front end 11 of the guide wire 10 is hook-shaped, but it may also extend straightly. The thickness of the guide wire is e.g. 1 mm, it may be as long as e.g. 30 cm and more.

The guide wire 10 is provided with a plurality of mutually spaced color marks 12 forming rings which are visible from each peripheral point of the guide wire. The length of the color marks is e.g. in the order of 2 mm.

The color marks are produced by an inductive heating means 13, which for inst. consists of an annular coil 14 through which the guide wire 10 is passed. If a point to be provided with a color mark 12 is just inside the coil 14, the guide wire is arrested to inductively heat said point. Coil 14 contains a number of turns which form a primary winding to be connected to a current source. The wire turns of the guide wire form the secondary winding in which currents of a high intensity are produced thus performing a selective heating of the guide wire section present in the coil.

The following Table I indicates the temper colors resulting from the stated temperatures in case of normal steel qualities:

| TABLE I |
|---|
| 200° C. - white yellow |
| 220° C. - straw yellow |
| 230° C. - golden yellow |
| 240° C. - yellow brown |
| 250° C. - brown red |
| 260° C. - red |
| 270° C. - purple |
| 280° C. - violet |
| 290° C. - dark blue |
| 300° C. - cornflower blue |
| 320° C. - bright blue |
| 340° C. - blue grey |
| 360° C. - grey |

In case of high alloy steels, the stated temper colors are visible but only at higher temperatures. In fact, the tempering time has an influence on the temper colors in that a longer tempering at a low temperature gives the same temper color as does shorter tempering at a higher temperature.

The inductive heating device 13 may be controlled by a (non-illustrated) temperature sensor or by a radiation sensor which is responsive to a selective color of the color marks 12, in order to set the desired color. It is also possible to constantly connect the inductive heating device 13 and to control the advance movement of the guide wire responsive to the temperature or to the achieved temper color.

While the invention has been described in its preferred embodiments, it is to be understood that the words which have been used are words of description rather than limitation and that changes may be made within the purview of the appended claims without departing from the true scope and spirit of the invention in its broader aspects.

We claim:

1. A catheter guide wire comprising:
   an elongated flexible body defining a smooth outer surface;
   the surface having at least one indicia extending along a predetermined length thereof;
   the smooth surface continuing throughout the predetermined portion along which the indicia extends; and
   the indicia being disposed a predetermined distance from a distal end of the body and being spaced regularly along the wire for indicating the length of said wire; and
   wherein said indicia are temper colors of steel.

2. A catheter guide wire as in claim 1, wherein said wire comprises an elongated strand of at least one spirally wound wire.

3. A guide wire as in claim 2, wherein adjacent turns of said spirally wound wire are in contact; and, further comprising a core disposed within said spirally wound wire.

4. The catheter guide wire as in claim 2, wherein a front end of the guide wire may be hook-shaped.

5. The catheter guide wire as in claim 2, wherein a front end of the guide wire may be straight.

6. The catheter guide wire as in claim 2, wherein the length of said indicia is about 2 mm.

7. The catheter guide wire as in claim 1, wherein said wire is chosen from the group comprising steel.

8. The catheter guide wire as in claim 1, wherein the guide wire has a thickness of 1 mm and a length of at least 30 cm.

9. The catheter guide wire as in claim 1, wherein said indicia are visible from each peripheral point of the guide wire.

10. A catheter guide wire comprising:
    an elongated flexible body defining a smooth outer surface;
    the surface having at least one indicia extending along a predetermined length thereof;
    the smooth surface continuing throughout the predetermined portion along which the indicia extends; and
    the indicia being disposed a predetermined distance from a distal end of the body and being spaced regularly along the wire for indicating the length of said wire; and
    said indicia are formed at a temperature range of 200 to 300 degrees Celsius.

11. A catheter guide wire comprising:
    an elongated flexible body defining a smooth exterior surface;
    the surface having at least one indicia extending along a predetermined portion thereof;
    the smooth surface extending throughout the predetermined portion along which the indicia extends;
    the indicia being disposed a predetermined distance from a distal end of the body;
    the body comprising a strand of at least one spirally wound wire about a core;
    the spirally wound wire and the core chosen from the group comprising steel;
    the body having a thickness of 1 mm, a length of at least 30 cm and a hook-shaped end; and
    the indicia chosen from the temper colors of steel and being visible from each peripheral point of the guide wire.

* * * * *